US005670619A

United States Patent [19]

Griesbacher et al.

[11] Patent Number: 5,670,619
[45] Date of Patent: Sep. 23, 1997

[54] BRADYKININ-ANTAGONISTS FOR THE TREATMENT OF ACUTE PANCREATITIS

[75] Inventors: Thomas Griesbacher, Hitzendorf; Fred Lembeck, Graz, both of Austria

[73] Assignee: Hoechst Aktiengesellschaft, Frankfurt am Main, Germany

[21] Appl. No.: 232,338

[22] Filed: Apr. 22, 1994

Related U.S. Application Data

[63] Continuation of Ser. No. 992,096, Dec. 17, 1992, abandoned.

[30] Foreign Application Priority Data

Dec. 21, 1991 [EP] European Pat. Off. ............ 91 122 055

[51] Int. Cl.$^6$ .............................. A61K 38/08; C07K 7/18
[52] U.S. Cl. .............................. 530/314; 530/328; 514/16
[58] Field of Search ...................................... 530/328, 314; 514/16

[56] References Cited

U.S. PATENT DOCUMENTS

| | | | |
|---|---|---|---|
| 4,693,993 | 9/1987 | Stewart et al. | 530/328 |
| 4,801,613 | 1/1989 | Stewart et al. | 530/328 |
| 4,923,963 | 5/1990 | Stewart et al. | 530/328 |
| 5,162,497 | 11/1992 | Coy et al. | 530/328 |

FOREIGN PATENT DOCUMENTS

| | | |
|---|---|---|
| 3943189 | 5/1990 | Australia . |
| 39431/89 | 6/1991 | Australia . |
| 0009010 A1 | 3/1980 | European Pat. Off. . |
| 0370453 A2 | 5/1990 | European Pat. Off. . |
| 0413277 A1 | 2/1991 | European Pat. Off. . |
| 0 451 791 A2 | 10/1991 | European Pat. Off. . |
| 3938751A1 | 5/1990 | Germany . |
| 90/6381 | 8/1990 | South Africa . |
| WO 86/07263 | 12/1986 | WIPO . |
| WO 89/01781 | 3/1989 | WIPO . |
| WO 89/09231 | 10/1989 | WIPO . |
| WO 91/09055 | 12/1990 | WIPO . |

OTHER PUBLICATIONS

Masuda, T., Chem. Abstracts 114:207931 (1991).
Leach, "Perspectives on Acute Pancreatitis", Scand J. Gasteroenterol, 27, Suppl, 192: 29–38. (1992).
Griesbacher et al, "Effects of the bradykinin antagonist, HOE 140, in experimental acute pancreatitis", Br. J. Pharmacol. 107, 356–360, 1992.
Knolle et al., "New and Highly Potent Bradykinin Antagonists," Proceedings of the 12th American Peptide Symposium, Jun., 1991, Cambridge, Mass., USA.
Smith et al., eds., 1992, pp. 113–114.
Wada et al., "Studies on Plasma Bradykinin Level in Rats with Experimental Acute Pancreatitis," Biological Abstracts, 90 (3):242 (1990).
Thompson, A.G., "Proteinase Inhibitors in Experimental and Clinical Pancreatitis", Chem. Abs. 69:85345p (1968).
Ohlsson et al., "Trypsin–induced release of bradykinin and of C3 fragments in man: clinical and experimental studies on the protective role of alpha–2–macroglobulin and aprotinin," Chem. Abs. 99:63645d (1983).
A.V. Suvernev, "On the Pathogenic Treatment of Acute Pancreatitis," Vestnik Khirurgii,126 (1):36–40 (1981).
Berg et al., Kinin Antagonist Does Not Protect Against the Hypotensive Response to Endotoxin, Anaphylaxis or Acute Pancreatitis. J. Pharmacology & Exp. Therapeutics, vol. 251 (2): 731–734 (1989).
Kyle et al., Probing the Bradykinin Receptor: Mapping the Geometric Topography Using Ethers of Hydroxyproline in Novel Peptides, J. Med. Chem., Vol. 34: 2649–2653 (1991).

*Primary Examiner*—Cecilia J. Tsang
*Assistant Examiner*—Anish Gupta
*Attorney, Agent, or Firm*—Finnegan, Henderson, Farabow, Garrett & Dunner, L.L.P.

[57] ABSTRACT

The invention relates to the use of bradykinin-antagonists of the formula

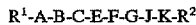

$R^1$-A-B-C-E-F-G-J-K-$R^2$ wherein $R^1$ represents hydrogen, $C_1$–$C_4$-alkanoyl which can be substituted by mercapto, hydroxyphenyl, (4-benzoyl) phenoxy or represents (4-benzoyl)benzoyl-Lys; A represents D-Arg or D-Lys or stands for a direct bond; B represents Arg which can be substituted by $NO_2$ or toluol-4-sulfonyl or represents Lys which can be substituted by toluol-4-sulfonyl or CO—NH—$C_6H_5$, or stands for a direct bond; C represents Hyp-Pro-Gly, Pro-Hyp-Gly, Pro-Pro-Gly or dehydroPro-Hyp-Gly; E represents Thi, Phe, Leu or Cha; F represents Ser or Cys; G represents D-Tic, D-Phe or D-Hyp substituted by $C_1$–$C_4$-alkoxy; J represents Tic, Aoc or Oic; K represents Arg or Ahx or stands for a direct bond; $R^2$ is hydroxy or amino; and the physiologically tolerable salts thereof for the treatments of acute pancreatitis, to pharmaceutical agents containing them and to the use thereof for the preparation of appropriate pharmaceutical compositions.

5 Claims, No Drawings

BRADYKININ-ANTAGONISTS FOR THE TREATMENT OF ACUTE PANCREATITIS

This application is a continuation of application Ser. No. 07/992,096 filed Dec. 17, 1992, now abandoned.

The invention relates to the use of bradykinin-antagonists or the physiologically tolerated salts thereof for the treatments of acute pancreatitis, to pharmaceutical agents containing them and to the use thereof for the preparation of appropriate pharmaceutical compositions.

Bradykinin has long been thought to participate in acute pancreatitis. In 1989 however, Berg et. al. have defeated this hypothesis. Berg et al. have demonstrated (The Journal of Pharmacology and Experimental Therapeutics, Vol. 251, No. 2 (1989) p. 731–734) that hypotension caused by development of acute pancreatitis in rats was not influenced by D-Arg$^0$-Hyp$^3$-Thi$^{5,8}$-D-Phe$^7$-BK (D-Arg-Arg-Pro-Hyp-Gly-Thi-Ser-D-Phe-Thi-Arg).

Surprisingly, we have found that peptides suitable for the treatment of acute pancreatitis are those of the formula I $$R^1\text{-A-B-C-E-F-G-J-K-R}^2 \qquad (I)$$

in which
- $R^1$ represents hydrogen, $C_1$–$C_4$-alkanoyl which can be substituted by mercapto, hydroxyphenyl, (4-benzoyl)phenoxy or represents (4-benzoyl)benzoyl-Lys;
- A represents D-Arg or D-Lys or stands for a direct bond;
- B represents Arg which can be substituted by $NO_2$ or toluol-4-sulfonyl or represents Lys which can be substituted by toluol-4-sulfonyl or CO—NH—$C_6H_5$, or stands for a direct bond;
- C represents Hyp-Pro-Gly, Pro-Hyp-Gly, Pro-Pro-Gly or dehydroPro-Hyp-Gly;
- E represents Thi, Phe, Leu or Cha;
- F represents Ser or Cys;
- G represents D-Tic, D-Phe or D-Hyp substituted by $C_1$–$C_4$-alkoxy;
- J represents Tic, Aoc or Oic;
- K represents Arg or Ahx or stands for a direct bond;
- $R^2$ is hydroxy or amino;
and their physiologically tolerable salts.

If not stated otherwise, the abbreviation of an amino acid radical or imino acid radical without a stereodescriptor stands for the radical in the L-form, such as, for example

- Ahx ε-Aminohexanoyl
- Aoc cis, endo-2-azabicyclo[3.3.0]octan-3-S-carbonyl
- Arg arginine
- Cha cyclohexylalanine
- Cys cysteine
- Gly glycine
- Hyp hydroxyproline
- HypE (transmethyl) 4-hydroxyproline-trans-methylether
- HypE(transpropyl) 4-hydroxyproline-trans-propylether
- Leu leucine
- Lys lysine
- Oic cis, endo octahydroindole-carbonyl
- Phe phenylalanine
- Pro proline
- Thi 2-thienylalanine
- Tic 1,2,3,4-tetrahydroisochinoline-3-yl-carbonyl
- Tyr tyrosine Some of the said amino acid radicals or imino acid radicals are described in EP-A 370 453 (HOE 88/F 328K).

A preferred embodiment comprises use of the peptides of the formula I, in which
- $R^1$ represents hydrogen, acetyl which can be substituted by mercapto or (4-benzoyl)phenoxy or represents (4-benzoyl)benzoyl-Lys;
- A represents D-Arg or stands for a direct bond;
- B represents Arg which can be substituted by toluol-4-sulfonyl or stands for a direct bond;
- C represents Pro-Hyp-Gly, Pro-Pro-Gly or dehydroPro-Hyp-Gly;
- E represents Thi, Phe or Leu;
- F represents Ser or Cys;
- G represents D-Tic, D-Phe, D-HypE(transmethyl) or D-HypE(transpropyl);
- J represents Tic, Aoc or Oic;
- K represents Arg; and
- $R^2$ is hydroxy;
and their physiologically tolerable salts.

A particularly preferred embodiment comprises use of the peptides of the formula I, in which
- $R^1$ represents hydrogen or (4-benzoyl)benzoyl-Lys;
- A represents D-Arg;
- B represents Arg;
- C represents Pro-Hyp-Gly or Pro-Pro-Gly;
- E represents Thi, Phe or Leu;
- F represents Ser;
- G represents D-Tic or D-HypE(transpropyl);
- J represents Oic;
- K represents Arg; and
- Y is hydroxy;
and their physiologically tolerable salts.

Very particularly preferred is the use of the following peptides of the formula I H-D-Arg-Arg-Pro-Hyp-Gly-Thi-Ser-D-Tic-Oic-Arg-OH, H-D-Arg-Arg-Pro-Pro-Gly-Thi-Ser-D-Tic-Oic-Arg-OH, H-D-Arg-Arg-Pro-Hyp-Gly-Phe-Ser-D-Tic-Oic-Arg-OH, H-(4-benzoyl)benzoyl)Lys-D-Arg-Arg-Pro-Hyp-Gly-Thi-Ser-D-Tic-Oic-Arg-OH, H-D-Arg-Arg-Pro-Hyp-Gly-Leu-Ser-D-Tic-Oic-Arg-OH, H-D-Arg-Arg-Pro-Hyp-Gly-Phe-Ser-D-HypE(transpropyl)-Oic-Arg-OH and their physiologically tolerable salts.

The peptides of the formula I can be prepared for example, by
- a) reacting a fragment having a C-terminal free carboxyl group or its activated derivative with an appropriate fragment having an N-terminal free amino group or
- b) synthesizing the peptide stepwise, optionally splitting off one or more protective groups temporarily introduced for the protection of other functions in the compound obtained according to (a) or (b) and optionally converting the compounds of the formula I thus obtained into their physiologically tolerable salts or as described in EP-A 370 453 (HOE 88/F 328K), EP-A 413 277 (HOE 89/F 261), EP-A 455 133 (HOE 90/F 131) or in Journal of Medicinal Chemistry, 1991, Vol. 34, No. 8, pages 2649–2653.

The peptides of the formula I can easily be converted with alkali metals, alkaline earth metals, physiologically tolerable amines and inorganic or organic acids such as, for example, HCl, HBr, $H_2SO_4$, $H_3PO_4$, maleic acid, fumaric acid, citric acid, tartaric acid and acetic acid, into the corresponding salts. The salts can be used according to the invention.

The peptides of the formula I are useful in the treatment of acute pancreatitis which is characterized by a massive oedema of the gland and the retroperitoneal tissue, interstitial activation of proteolytic enzymes, elevation of serum amylase and lipase levels, hypovolaemia, hypoalbuminaemia, pulmonary oedema and severe pain.

Experimental Tests:

Substances: A peptide of the formula I, caerulein (CRL, Sigma, U.S.A.) and bradykinin (Bachem, Switzerland) were dissolved in physiological saline at a concentration of 1 mM. Porcine pancreatic kallikrein (Sigma, U.S.A.) was dissolved in 50% (v/v) ethanol and diluted with a 154 mM solution of NaCl. Pentobarbitone sodium (®Nembutal) was purchased from Sanofi (France). Phenobarbitone sodium was obtained from Apoka (Austria) and dissolved freshly each day at a concentration of 80 mg/ml in a 154 mM sodium chloride solution. Captopril was obtained from Squibb von Heyden GmbH (Austria). Evans blue was purchased from Sigma (U.S.A.).

Peptide of the formula I (tables 1–3):

A: H-D-Arg-Arg-Pro-Hyp-Gly-Thi-Ser-D-Tic-Oic-Arg-OH

Statistical Analysis: The hypotensive effects of bradykinin and kallikrein in the rabbit before and after a peptide of the formula I were compared using the Quade test (Conover W. J.: "Practical nonparametric statistics", 2nd ed. New York, Wiley, 1980, 295–299). Comparisons between the 4 treatment groups in the rat were made by nonparametric multiple comparisons (Zar J. H.: "Biostatistical analysis", 2nd ed. Englewood Cliffs, Prentice-Hall, 1984).

1. Evidence for the inhibition of endogeneously formed bradykinin:

Methods: Rabbits of either sex (3.5–5.0 kg) were anaesthetized with pentobarbitone sodium (35 mg/kg i.v.). Arterial blood pressure was monitored in a carotid artery using a Statham pressure transducer. I.v. injections of bradykinin (1 to 10 nmol/kg) or kallikrein (1 to 10 U/kg) were made into a jugular vein at intervals of 10 min. A peptide of the formula I (3 nmol/kg) was given i.v. and the injections of bradykinin or kallikrein were then repeated.

Results: The short fall in blood pressure evoked by bradykinin and kallikrein, even in doses of 10 nmol/kg bradykinin and 10 U/kg kallikrein, respectively, were completely blocked by treatment with the peptide A. The results demonstrate clearly that not only injected bradykinin but also bradykinin split off from kininogen by kallikrein is completely inhibited by the peptide of the formula I (peptide A).

2. Treatment of experimental pancreatitis in rats:

General methods: To induce experimental pancreatitis in animals, a number of procedures have been used including ligation of the pancreatic duct, injection of bile salts into the pancreatic duct, infusion of oleic acid, or infusion of the amphibian cholecystokinin analogue, caerulein. The latter procedure produces a hyperstimulation of the exocrine function of the pancreas and leads to morphological changes that share many features also seen in human acute pancreatitis (Willemer S., Bialek R., Köhler H. Adler G.; "Caerulein-induced acute pancreatitis in rats: changes in glycoprotein-composition of subcellular membrane systems in acinar cells;" Histochemistry 1990; 95; 87–96). Caerulein-induced pancreatitis in rats was used for the following experiments.

Effects in rat blood pressure:

Method: Female Sprague-Dawley rats (260±30 g) were anaesthetized with pentobarbitone sodium (40 mg/kg, i.p.) and phenobarbitone sodium (160 mg/kg, i.p.). Captopril (50 mol/kg, i.p.) was injected at the same time to augment the actions of released kinins by inhibition of kininase II which is active in many tissues (Lembeck F., Griesbacher T., Eckhardt M.; "Demonstration of extrapulmonary activity of angiotensin converting enzyme in intact tissue preparations;" Br. J. Pharmacol. 1990, 100, 49–54). 10 min later, the animals were given a s.c. injection of a peptide of the formula I (100 nmol/kg) or of a corresponding volume (0.5 ml/kg) of a 154 mM sodium chloride solution. The systemic arterial blood pressure was monitored in a carotid artery using a Statham pressure transducer. A jugular vein was cannulated to allow the infusion of either caerulein (4 nmol/kg/h) or of physiological saline (0.034 ml/min). The infusion was started 30 min after the s.c. injection of a peptide of the formula I or saline, and lasted for 2 h. At the end of the experiment the animals were killed by decapitation; the blood was collected for the determination of serum amylase and lipase.

Results: I.v. infusion of caerulein (4 nmol/kg/min) induced a reduction in blood pressure. The corresponding values obtained from animals treated with a peptide of the formula I (100 nmol/kg, s.c. 30 min before the onset of the infusion of caerulein) and those obtained in controls are given in table 1:

TABLE 1

| | Blood pressure | |
|---|---|---|
| Treatment by A | Infusion 0–120 min | Fall in blood pressure 40–105 min after start of CRL infusion |
| No | NaCl | 16 ± 3 |
| No | CRL | 38 ± 4 |
| Yes | NaCl | 13 ± 1 |
| Yes | CRL | 16 ± 4 |

Mean values ± SEM. Significance of difference between the groups indicated by brackets:
*P < 0.02;
**P < 0.01;
n.s. = not significant;
n = 10 for each group;

The result demonstrates that CRL induced fall in blood pressure has been reduced by treatment with the peptide A to the magnitude of control values. Treatment with the peptide A without infusion of CRL did not differ from the NaCl-infusion as control.

Effects on pancreatic oedema:

Method: Quantification of the pancreatic oedema was achieved by measuring the dry weight of pancreas and the accumulation of plasma proteins in pancreas. At the end of the infusions (see blood pressure experiments), the blood was collected for measuring enzymes in serum. The pancreas was excised and weighed. After drying the tissue, the difference between wet and dry weight, in relation to dry weight, was used as a measure for the water content of the tissue. 5 mg/kg of Evans blue, which quantitatively binds to serum albumin (Rawson R. A.: "The binding of T-1824 and structurally related diazo dyes by plasma proteins", Amer. J. Physiol. 1943, 138, 708–717) was injected i.v. immediately before the start of the i.v. infusion of caerulein or physiological saline. Thereafter the pancreatic tissue was used to measure Evans blue concentration photometrically (Gamse R., Holzer P., Lembeck F.: "Decrease of substance P in primary afferent neurones and impairment of neurogenic plasma extravasation by capsaicin", Br. J. Pharmacol. 1980, 68, 207–213; Saria A., Lundberg J. M.: "Evans blue fluorescence: quantitative and morphological evaluation of vascular permeability in animal tissues", J. Neurosci. Meth. 1983, 8, 41–49). Control animals were treated with corresponding volumes of saline instead of a peptide of the formula I or caerulein. Plasma extravasation was quantified as content of water and Evans blue in the pancreas.

TABLE 2

Results:
Pancreatic oedema in rats

| A [sc.] | CRL [iv.] | water [g/g dry wgt] | Evans blue [µg/g dry wgt] |
|---|---|---|---|
| No | No | 2.50 ± 0.24 | 16.96 ± 3.26 |
| No | Yes | 7.28 ± 0.61 | 478.51 ± 79.94 |
| Yes | No | 2.62 ± 0.23 | 20.31 ± 5.80 |
| Yes | Yes | 3.11 ± 0.33 | 18.21 ± 4.24 |

Mean values ± SEM. Significance of difference between the groups indicated by brackets:
*P < 0.05;
**P < 0.01;
***P < 0.001;
n = 10 in each group;

Treatment by peptide A completely inhibited the CRL induced pancreatic oedema.

Influence on concentrations of pancreatic enzymes in serum:

Methods: Serum amylase was determined using a kinetic colour test with 2-chlor-4-nitrophenyl-D-maltoheptoside (Amylase test kit Roche, F.R.G.). Serum lipase was measured by the reduction of the turbidity due to cleavage of triolein to monoglyceride and oleic acid (Monotest Lipase, Boehringer Mannheim, F.R.G.). The detection limits for amylase and lipase were 11 U/l and 16 U/l, respectively. Control animals were treated with corresponding volumes of saline instead of a peptide of the formula I.

TABLE 3

Results:
Serum enzyme activities in rats

| A [sc.] | CRL [iv.] | Amylase [U/ml] | Lipase [U/ml] |
|---|---|---|---|
| No | No | 2.95 ± 0.29 | nn |
| No | Yes | 10.40 ± 1.14 | 1.51 ± 1.14 |
| Yes | No | 3.19 ± 0.21 | nn |
| Yes | Yes | 57.17 ± 16.11 | 16.33 ± 4.50 |

Means values ± SEM. Significance of difference between the groups indicated by brackets:
*P <0 0.05;
n = 6 in each group;
nn = not detectable.

Treatment by peptide A significantly potentiated the CRL-induced increases of amylase and lipase activities in blood pressure.

In summary, it has been shown that during CRL-induced experimental pancreatitis bradykinin is released. Bradykinin induce hypotension and pancreatic oedema. CRL causes also an increase of pancreatic enzymes in serum. The peptides of the formula I prevent the bradykinin-induced oedema and thus allows the pancreatic enzymes to leave the tissue without hindrance. It therefore diminishes subsequent pathological events in the pancreas. Accordingly, the peptides of the formula I have been demonstrated to be useful in the treatment of acute pancreatitis.

Additionally D-Arg$^0$-HYP$^3$-Thi$^{5.8}$D-Phe$^7$-BK disclosed by Berg et al. (see page 1) has been tested in comparision with the peptide A. Both antagonists were given in two groups of rats under identical conditions 10 minutes after the outset of the infusion of caerulein. While the peptide A completely inhibited the increase of water and Evans blue content in the pancreas, the antagonist described by Berg et al. was completely ineffective when given in a dose 10 times higher than the peptide A.

The invention furthermore embraces the use of the peptides according to the invention for the preparation of pharmaceuticals used for the treatment of acute pancreatitis in mammals, such as humans etc.

The pharmaceuticals are prepared by processes known per se and familiar to the expert. As pharmaceuticals, the pharmacologically active compounds (=active substance) according to the invention are employed either as such or, preferably, in combination with suitable pharmaceutical auxiliaries in the form of solutions with the content of active substance being up to about 95%, preferably between 10 and 75%.

The auxiliaries suitable for the desired pharmaceutical formulation are familiar to the expert on the basis of his expert knowledge. Besides solvents and other active substance vehicles it is possible to use, for example, antioxidants, dispersing agents, preservatives or solubilizers.

The active substances can be administered parenterally, i.e. as subcutaneous, i.m. or i.v. injection or infusion. The dosage of the active substance depends on the mammal species, the body weight, age and on the manner of administration.

The pharmaceutical preparations of the present invention are prepared in solution using processes known per se.

For intravenous, subcutaneous or intramuscular administration, the active compounds or their physiologically tolerable salts, if desired with the pharmaceutically customary auxiliaries, for example for isotonisizing or adjusting pH, and solubilizers, emulsifiers or other auxiliaries, are brought into solution.

A suitable dose range for forms for all kinds of systemic administration is 0.01–1 mg/kg.

EXAMPLES

1. Solution for injection or infusion

| | |
|---|---|
| H—D—Arg—Arg—Pro—Hyp—Gly—Thi—Ser—D—Tic—Oic—Arg—OH | 5.00 mg |
| Acetic acid | 6.2 mg |
| Sodium acetate × 3 H$_2$O | 115.5 mg |
| Sodium chloride | 835.0 mg |
| Water for injections | ad 100.0 ml |

The solution is adjusted to pH 5.5.

2. Solution for injection or infusion

| | |
|---|---|
| H—D—Arg—Arg—Pro—Hyp—Gly—Thi—Ser—D—Tic—Oic—Arg—OH | 250.0 mg |
| Acetic acid | 6.2 mg |
| Sodium acetate ×3 H$_2$O | 115.5 mg |
| Sodium chloride | 835.0 mg |
| Water for injections | ad 100.0 ml |

The solution is adjusted to pH 5.5.

TABLE OF PEPTIDES

1
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic

| D-Arg | Arg | Pro | Hyp | Gly | Thy | Ser | D-Tic | Oic | Arg |
|---|---|---|---|---|---|---|---|---|---|
| Xaa | Arg | Pro | 3Hyp | Gly | Xaa | Ser | Xaa | Xaa | Arg |
| | | | | 5 | | | | | 10 |

2
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic

| D-Arg | Arg | Pro | Pro | Gly | Thi | Ser | D-Tic | Oic | Arg |
|---|---|---|---|---|---|---|---|---|---|
| Xaa | Arg | Pro | Pro | Gly | Xaa | Ser | Xaa | Xaa | Arg |
| | | | | 5 | | | | | 10 |

3
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic

| D-Arg | Arg | Pro | Hyp | Gly | Phe | Ser | D-Tic | Oic | Arg |
|---|---|---|---|---|---|---|---|---|---|
| Xaa | Arg | Pro | 3Hyp | Gly | Phe | Ser | Xaa | Xaa | Arg |
| | | | | 5 | | | | | 10 |

4
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic (4-Benzoyl)benzoyl)Lys D-Arg Arg Pro Hyp Gly Thi Ser D-Tic Oic Arg
Xaa Xaa Arg Pro 3Hyp Gly Xaa Ser Xaa Xaa

TABLE OF PEPTIDES-continued

```
Arg                                           5                                              10
5
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic
D-Arg            Arg      Pro     Hyp      Gly Leu Ser    D-Tic              Oic      Arg
Xaa              Arg      Pro     3Hyp     Gly Leu Ser    Xaa                Xaa      Arg
                                           5                                           10
6
SEQUENCE TYPE: amino acids (natural and unnatural)
SEQUENCE LENGTH: 10 amino acids
STRANDEDNESS: single
TOPOLOGY: linear
MOLECULE TYPE: peptide
ORIGINAL SOURCE: no
ORGANISM: no
IMMEDIATE EXPERIMENTAL SOURCE: synthetic
D-Arg            Arg      Pro     Hyp      Gly Phe Ser    D-HypE(transpropyl) Oic     Arg
Xaa              Arg      Pro     3Hyp     Gly Leu Ser    Xaa                 Xaa     Arg
                                           5                                           10
```

We claim:

1. A method of treating acute pancreatitis in a mammal in need of said treatment, said method comprising administering to said mammal a peptide, wherein said peptide is H-D-Arg-Arg-Pro-Hyp-Gly-Thi-Ser-D-Tic-Oic-Arg-OH or a physiologically tolerated salt thereof.

2. A method of treating acute pancreatitis in a mammal in need of said treatment, said method comprising administering to said mammal a peptide of the formula I, $R^1$-A-B-C-E-F-G-J-K-$R^2$ in which $R^1$ represents hydrogen, $C_2$–$C_4$-alkanoyl which can be substituted by mercapto, hydroxyphenyl, or (4-benzoyl)phenoxy or represents (4-benzoyl)benzoyl-Lys;

A represents D-Arg or D-Lys or strands for a direct bond;

B represents Arg which can be substituted by $NO_2$ or toluol-4-sulfonyl or represents Lys which can be substituted by toluol-4-sulfonyl or CO—NH—$C_6H_5$, or stands for a direct bond;

C represents Hyp-Pro-Gly, Pro-Hyp-Gly, Pro-Pro-Gly or dehydroPro-Hyp-Gly;

E represents Thi, Phe, Leu or Cha;

F represents Ser or Cys;

G represents D-Tic, D-Phe or D-Hyp substituted by $C_1$–$C_4$-alkoxy;

J represents Tic, Aoc or Oic;

K represents Arg or Ahx or stands for a direct bond;

$R^2$ is hydroxy or amino;

or a physiologically tolerated salt thereof.

3. The method of claim 2, wherein $R^1$ represents hydrogen, acetyl which can be substituted by mercapto or (4-benzoyl)phenoxy or represents (4-benzoyl)benzoyl-Lys;

A represents D-Arg or stands for a direct bond;

B represents Arg which can be substituted by toluol-4-sulfonyl or stands for a direct bond;

C represents Pro-Hyp-Gly, Pro-Pro-Gly or dehydroPro-Hyp-Gly;

E represents Thi, Phe or Leu;

F represents Ser or Cys;

G represents D-Tic, D-Phe or D-HypE (transpropyl);

J represents Tic, Aoc or Oic;

K represents Arg; and $R^2$ is hydroxy;

or a physiologically tolerated salt thereof.

4. The method of claim 3, wherein $R^1$ represents hydrogen or (4-benzoyl)benzoyl-Lys;

A represents D-Arg;

B represents Arg;

C represents Pro-Hyp-Gly or Pro-Pro-Gly;

E represents Thi, Phe or Leu;

F represents Ser;

G represents D-Tic or D-HypE (transpropyl);

J represents Oic;

K represents Arg; and $R^2$ is hydroxy;

or a physiologically tolerated salt thereof.

5. The method of claim 4, wherein said peptide is selected from:

H-D-Arg-Arg-Pro-Hyp-Gly-Thi-Ser-D-Tic-Oic-Arg-OH
    SEQ ID NO:1;

H-D-Arg-Arg-Pro-Pro-Gly-Thi-Ser-D-Tic-Oic-Arg-OH
    SEQ ID NO:2;

H-D-Arg-Arg-Pro-Hyp-Gly-Phe-Ser-D-Tic-Oic-Arg-OH SEQ ID NO: 3;

H-(4-benzoyl)benzoyl)Lys-D-Arg-Arg-Pro-Hyp-Gly-Thi-Ser-D-Tic-Oic-Arg-OH    SEQ ID NO: 4;

H-D-Arg-Arg-Pro-Hyp-Gly-Leu-Ser-D-Tic-Oic-Arg-OH
    SEQ ID NO: 5;

and

H-D-Arg-Arg-Pro-Hyp-Gly-Phe-Ser-D-HypE(transpropyl)-Oic-Arg-OH    SEQ ID NO: 6;

or a physiologically tolerated salt thereof.

* * * * *